US005999632A

United States Patent [19]

Leysieffer et al.

[11] Patent Number: 5,999,632
[45] Date of Patent: Dec. 7, 1999

[54] FIXATION ELEMENT FOR AN IMPLANTABLE MICROPHONE

[75] Inventors: Hans Leysieffer, Taufkirchen; Joachim W. Baumann, München; Rolf Martin Lehner, Esslingen; Gerd M. Müller, Unterschleissheim; Gabriele Reischl, München, all of Germany

[73] Assignee: IMPLEX Aktiengesellschaft Hearing Technology, Ismaning, Germany

[21] Appl. No.: 09/097,710

[22] Filed: Jun. 16, 1998

[30] Foreign Application Priority Data

Nov. 26, 1997 [DE] Germany .......................... 197 52 447

[51] Int. Cl.[6] .......................... H04R 25/02; H04R 25/00

[52] U.S. Cl. .......................... 381/328; 181/130; 181/135; 607/57; 623/10

[58] Field of Search .......................... 607/55, 57; 623/10; 181/130, 132, 135, 171, 172; 381/328, 364, 385

[56] References Cited

U.S. PATENT DOCUMENTS

| | | |
|---|---|---|
| 2,487,038 | 3/1949 | Baum . |
| 2,641,328 | 7/1953 | Beaudry . |
| 4,055,233 | 10/1977 | Huntress . |
| 4,744,792 | 5/1988 | Sander et al. . |
| 5,277,694 | 1/1994 | Leysieffer et al. . |
| 5,282,253 | 1/1994 | Konomi . |
| 5,572,594 | 11/1996 | Devoe et al. . |
| 5,881,158 | 3/1999 | Lesinski et al. . |

FOREIGN PATENT DOCUMENTS

| | | |
|---|---|---|
| PCT/US97/04740 | 3/1997 | WIPO . |

OTHER PUBLICATIONS

H. Leysieffer et al., HNO 45, Oct., 1997, Ein Implantierbares Mikrofon Für Elektronische Hörimplantate, pp. 816–827.

H.P. Zenner et al., HNO 45, Oct., 1997, Aktive Elektronische Hörimplantate Für Mittel—Und Innenohrschwerhörige—Eine Neue Ära Der Ohrchirurgie, pp. 749–757.

*Primary Examiner*—William E. Kamm
*Assistant Examiner*—Carl H. Layno
*Attorney, Agent, or Firm*—Sixbey, Friedman, Leedom & Ferguson; David S. Safran

[57] ABSTRACT

A fixation element secures to a patient's ear an implantable microphone having a cylindrical housing part with an acoustic inlet membrane after insertion into a hole which crosses a rear bony wall of the patient's auditory canal. The fixation element has a cylindrical sleeve part which surrounds the cylindrical housing part of the microphone and which has projecting, elastic flange parts which can be placed against the side of the wall of the auditory canal which faces the skin of the auditory canal. In use, the elastic flange parts are held in a bent position against an elastic restoring force of the flange parts, before implantation, by applying a holder to the flange parts which allows insertion of the flanges through the hole of the wall of the auditory canal. After the microphone assembly has been inserted through the hole, the holder (which can be, for example, thread or a cap) is removed allowing the elastic flange parts to spring into a position in which they project essentially radially away from the cylindrical sleeve part between the wall of the auditory canal which faces skin of the auditory canal and the skin of the auditory canal.

20 Claims, 5 Drawing Sheets

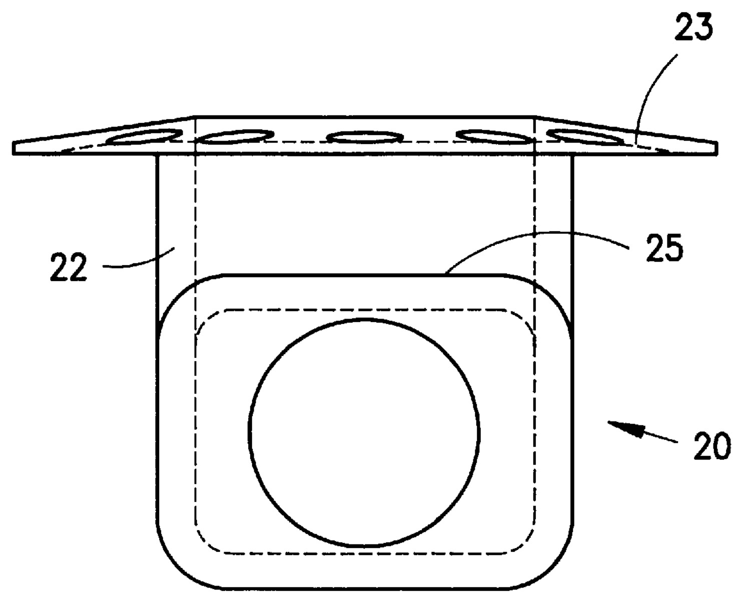
F/G. 2
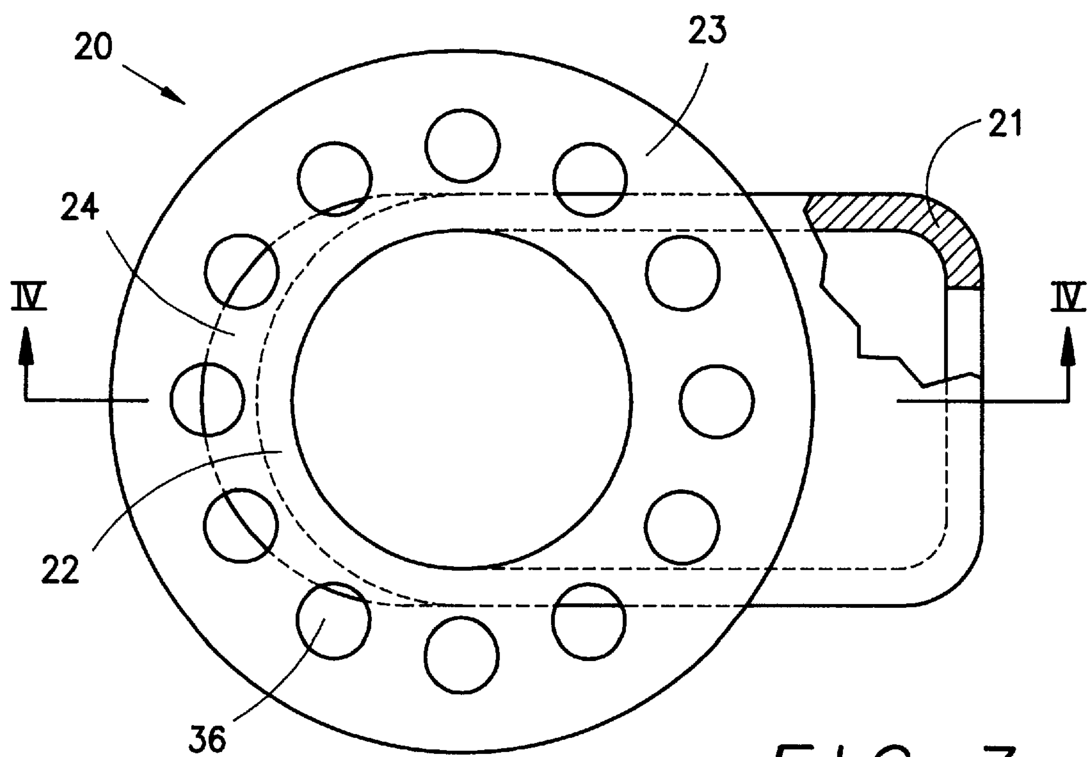
F/G. 3

FIXATION ELEMENT FOR AN IMPLANTABLE MICROPHONE

BACKGROUND OF THE INVENTION

1. Field of the Invention

The invention relates to a fixation element for an implantable microphone which, with a cylindrical housing part provided with an acoustic inlet membrane, can be inserted into a hole which crosses the rear bony wall of the auditory canal and which, for example, can form a component of a partially or fully implantable hearing aid.

2. Description of Related Art

One embodiment of a microphone of the aforementioned type is the subject of commonly owned U.S. patent application Ser. No. 08/816,633, filed Mar. 13, 1997, and is detailed in the article "An implantable microphone for electronic hearing implants" by H. Leysieffer et al., HNO 45: 816–827 (October 1997). It is known from this article that the microphone housing can be mechanically fixed in the mastoid using bone cement. However, fixing with cement engenders a number of problems. Under certain circumstances the bone cement can trigger undesirable side effects at the implantation site. Due to the restricted space conditions and unfavorable visual conditions, handling at the implantation site is difficult. Bone cement can also unwantedly reach locations where it is disruptive. Subsequent correction of the microphone location in the hole of the wall of the auditory canal is essentially precluded. Clinical experiments show that this is a problem due to the small thickness of the bony wall of the auditory canal. In addition, screws in the region of this implantation site are often felt to be painful even long after surgery.

SUMMARY OF THE INVENTION

A primary object of the present invention is to devise a fixation element for an implantable microphone which allows a much simplified and nevertheless highly precise implantation of the microphone, while avoiding the disadvantages associated with the use of bone cement.

This object is achieved with a fixation element for an implantable microphone which, with a cylindrical housing part provided with an acoustic inlet membrane, can be inserted into a hole which crosses the rear bony wall of the auditory canal and which, for example, can form a component of a partially or fully implantable hearing aid and which, according to the invention, has a sleeve which surrounds the microphone housing part and which has a projecting, elastic flange part which can be placed against the side of the wall of the auditory canal facing the skin of the auditory canal.

The fixation element of the invention makes it possible to easily clip the microphone housing into the hole which traverses the rear bony wall of the auditory canal. Use of bone cement is avoided. The flange parts which adjoin the bony wall of the auditory canal provide for exact alignment of the microphone housing with reference to the wall of the auditory canal. Together with the cylindrical sleeve part which engages the wall of the hole they ensure secure holding of the implanted microphone with long term stability.

In another embodiment of the invention, the sleeve is provided with other projecting flange parts which can be placed against the side of the bony wall of the auditory canal facing away from the skin of the auditory canal. In this way, retention of the microphone in the implanted state is further improved. Furthermore, unintentional tilting of the microphone housing relative to the wall of the auditory canal during the implantation process or later is reliably precluded.

Preferably the entire sleeve is made from biocompatible elastic material which is suitably chosen from the group consisting of silicones and polyurethanes. This material allows limited deformation of the sleeve when inserted into the hole of the bony wall of the auditory canal. It also enables the flange parts to rest easily against the associated side of the wall of the auditory passage. In the region of the cylindrical sleeve part, clamping force can be easily provided.

In another embodiment of the invention, the sleeve can be part of a casing which, at least for the most part, and preferably entirely, surrounds the microphone except for the acoustic inlet membrane. In this way, an especially secure anchoring of the sleeve with reference to the microphone housing is achieved.

The flange parts which, in the implanted state, are designed to rest against the side of the wall of the auditory canal wall facing the skin of the auditory canal can, during implantation, be kept by a tool in a position in which they can be inserted through the hole of the wall of the auditory canal. However, Implanting of the microphone is especially simple if, in a development of the invention, there is a holder which holds the flange parts, which can be placed against the side of the wall of the auditory canal facing the skin of the auditory canal, before implantation against an elastic reset force of the flange parts in a bent position which allows insertion through the hole of the wall of the auditory canal. In doing so, the flange parts which can be placed against the side of the wall of the auditory canal facing the skin of the auditory canal are preferably composed and dimensioned such that, after removal of the holder, they spring into a position in which they project essentially radially away from the cylindrical sleeve part. In this form of the fixation element, the surgeon need only insert the cased cylindrical housing part of the microphone together with the holder into the hole of the rear bony wall of the auditory canal and then remove or deactivate the holder to provide for an exact and secure seating of the microphone at the implantation site.

As a holder, for example, there can simply be a thread which can be severed in the course of implantation and which first holds the flange parts in a position which does not disrupt implantation and which subsequently allows the flange parts, based on their elastic properties, to pass into a relieved state in which they assume their holding function. According to one advantageous modified embodiment, a cap can be placed on the bent flange parts as the holder.

According to another embodiment of the invention, the flange parts which can be placed against the side of the wall of the auditory canal facing the skin of the auditory canal are angled, proceeding from the cylindrical sleeve part, in the direction to this sleeve part. This contributes to flange parts resting faultlessly against the side of the wall of the auditory canal facing the skin of the auditory canal, even if the surface of the auditory canal has a certain unevenness due to anatomical circumstances. For the same reason, the wall thickness of the flange parts which can be placed against the side of the wall of the auditory canal facing the skin of the auditory canal preferably decreases in a radially outward direction.

The flange parts which can be placed against the side of the wall of the auditory canal facing the skin of the auditory canal can in particular be made as an annular flange which projects essentially radially in the relieved state away from the cylindrical sleeve part. However, basically, other geometrical configurations are possible if only, on the one hand, the necessary retaining function is ensured, and on the other hand, the flange parts easily find room in the space between the skin of the auditory canal and the wall of the auditory canal.

Preferably, the flange parts which can be placed against the side of the wall of the auditory canal facing the skin of the auditory canal are provided with openings which are designed especially to enable passage of nutrients between the bony wall of the auditory canal and the skin of the auditory canal in the region of the annular flange.

It goes without saying that the fixation element of the invention is suitable essentially for microphones of any form, for example, for microphones with a continuously cylindrical housing. But, if the microphone in the conventional manner (article "An implantable microphone for electronic hearing implants" by H. Leysieffer et al., HNO 45: 816–827 (October 1997)) is provided with a multi-leg microphone housing, in which the first housing leg forms the cylindrical housing part and the second housing leg is set back by a distance corresponding to roughly the thickness of the rear bony wall of the auditory canal relative to the plane of the acoustic inlet membrane, the second housing leg itself, or the part of the fixation element which jackets the second housing leg, forms at least some of the flange parts which can be placed against the side of the wall of the auditory canal facing away from the skin of the auditory canal. Here, a collar which projects on the side diametrically opposite the second housing leg from the cylindrical sleeve part is included among the flange parts which can be placed against the side of the wall of the auditory canal facing away from the skin of the auditory canal.

Feasibley, at least one sleeve is produced from a material with a Shore A hardness of 20 to 70.

These and further objects, features and advantages of the present invention will become apparent from the following description when taken in connection with the accompanying drawings which, for purposes of illustration only, show several embodiments in accordance with the present invention.

BRIEF DESCRIPTION OF THE DRAWINGS

FIG. 2 is an enlarged view of the fixation element provided on the microphone as shown in FIG. 1 in the viewing direction of arrow A therein;

FIG. 3 is a plan view of the fixation element shown in FIG. 2;

DETAILED DESCRIPTION OF THE PREFERRED EMBODIMENTS

Figure 1:
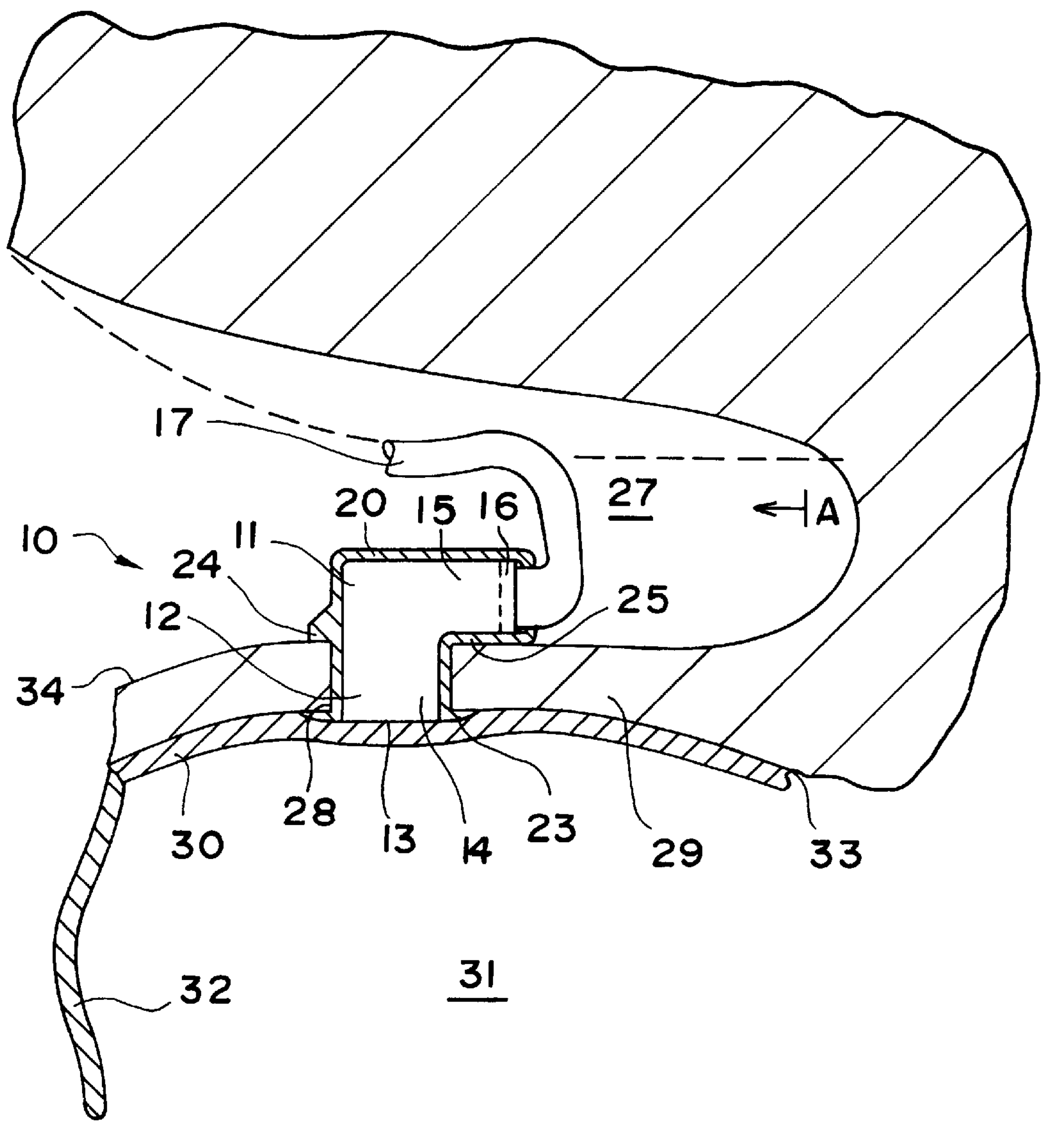
FIG. 1 is a schematic cross-sectional view of a microphone which is implanted into the rear bony wall of the auditory canal and which is held by means of a fixation element in accordance with a preferred embodiment of the present invention.

FIG. 1 schematically shows a microphone 10 which can be a component of a partially or fully implantable hearing aid. The hearing aid, as such, can be made in a conventional manner. Examples of applicable hearing aids are detailed in the article "Active electronic hearing implants for middle and inner ear hearing impaired—a new era in ear surgery" by H. P. Zenner et al. HNO 45: 749–757 (October 1997). Microphone 10 has an angular microphone housing 11 having two legs at a right angle relative to each other, and is shown only schematically in FIG. 1 for the sake of simplicity, and therefore, is not illustrated in cross section. In first leg 12 of microphone housing 11, a microphone capsule (electromechanical transducer) is accommodated; leg 12 forms a cylindrical housing part 14 provided with an acoustic membrane 13 at the inner end thereof. The second housing leg 15 accommodates an electrical bushing 6 for an electric feed line 17.

Microphone 10 is equipped with a fixation element 20 which, in the illustrated embodiment, forms a casing which accommodates the entire microphone housing 11. Part of fixation element 20, as is shown in particular in FIGS. 2–5, is a sleeve 21 which with cylindrical sleeve part 22 surrounds cylindrical housing part 14. Sleeve 21, furthermore, includes flange parts 23, 24 and 25 which project radially outwardly on both axial ends of cylindrical sleeve part 22.

According to FIG. 1, cylindrical housing part 14, together with cylindrical sleeve part 22, can be inserted from mastoid cavity 27 into a hole 28 which crosses the rear bony wall 29 of the auditory canal 31. In FIG. 1, the auditory canal 31 is shown lined with skin 30 and the eardrum is labeled 32. Dimensioning is such that, in the implanted state of microphone 10, flange parts 23, 24, and 25, on the one hand, rests against the side 33 of the wall 29 of the auditory canal 31 that faces skin 30, and on the other hand, against the side 34 of wall 29 that faces away from the skin 30 of the auditory canal. In doing so, the acoustic membrane 13 comes into direct contact with the skin 30 of the auditory canal 31.

Accordingly, the axial distance a (FIG. 4) that exists between the flange part 23 and the flange parts 24 and 25 conforms with the average wall thickness of bony wall 29 of the auditory canal 31. Distance a is generally in the range between 1.0 and 2.5 mm, and preferably, it is roughly 1.6 mm. Acoustic membrane 13, in the interest of good contact with skin 30 of the auditory canal, preferably, has a diameter that is less than 5.0 mm. For example, cylindrical housing part 14, accordingly, has an outside diameter of roughly 4.5 mm and cylindrical sleeve part 22 has an outside diameter of roughly 5.3 mm.

In the embodiment of fixation element 20 shown in FIGS. 1–6, flange part 23, which is essentially flush with acoustic membrane 13, is made as an annular flange which, in the released, i.e., unstressed, state projects essentially radially away from the end of cylindrical sleeve part 22 on the auditory canal side. Annular flange 23 is provided with a sequence of openings 36 which are distributed in the peripheral direction. The purpose of openings 36 is mainly to allow transport of nutrients between bony wall 29 and skin 30 of the auditory canal 31 in the region of annular flange 23. The shape and number of openings 36 are unimportant as long as the openings satisfy this purpose and the necessary mechanical strength of annular flange 23 is maintained.

Before implantation, surgical thread 37 (FIG. 6) is threaded through the sequence of openings 36 and temporarily fixed by twisting, knotting or the like in a state in which annular flange 23 is together and away from flange parts 23 and 24 in the axial direction. In this form, the cylindrical housing part 14 is surrounded by cylindrical sleeve part 22 and can be inserted through hole 28 in wall 30 of the auditory canal 31. Then, if thread 37 is severed, the annular flange 23 returns to its relieved state shown in FIGS. 1–4. To induce this process, at least the part of fixation element 20 which forms annular flange 23 is made elastic.

In the implanted state (FIG. 1), the annular flange 23 should be nestled as close as possible to the side 33 of the wall 30 of the auditory canal which faces the skin 30 of the auditory canal, in spite of the unevenness of this wall surface. To promote this, in addition to a suitable choice of materials for at least annular flange 23, in the embodiment shown, there are three measures which can be seen especially clearly from FIG. 5. On the one hand, the wall thickness of annular flange 23 is reduced in thickness (relative to the sleeve part 22) as much as possible without adversely affecting the retaining function of the annular flange. Furthermore, annular flange 23, proceeding from the cylindrical sleeve part 22, is angled in the direction toward flange parts 24, 25. Finally, the wall thickness of annular flange 23 is tapered, decreasing in a radially outward direction. The wall thickness of annular flange 23 can feasibly be reduced from roughly 0.1 mm to 0.2 mm near sleeve part 22 to roughly 0.03 to 0.01 mm at the outside edge of annular flange 23. The angle $\alpha$ at which the annular flange 23 is inclined toward flanges 24, 25, can be in the range from 0 to 20 degrees, and preferably is about 5 degrees.

Flange part 25 is formed by part of the casing (fixation element 20) which overlaps the side of housing leg 15 facing annular flange 23. Flange part 24 is a collar which projects from cylindrical sleeve part 22 on the side diametrically opposite housing leg 15 (see especially FIGS. 3 and 4).

Figure 4:
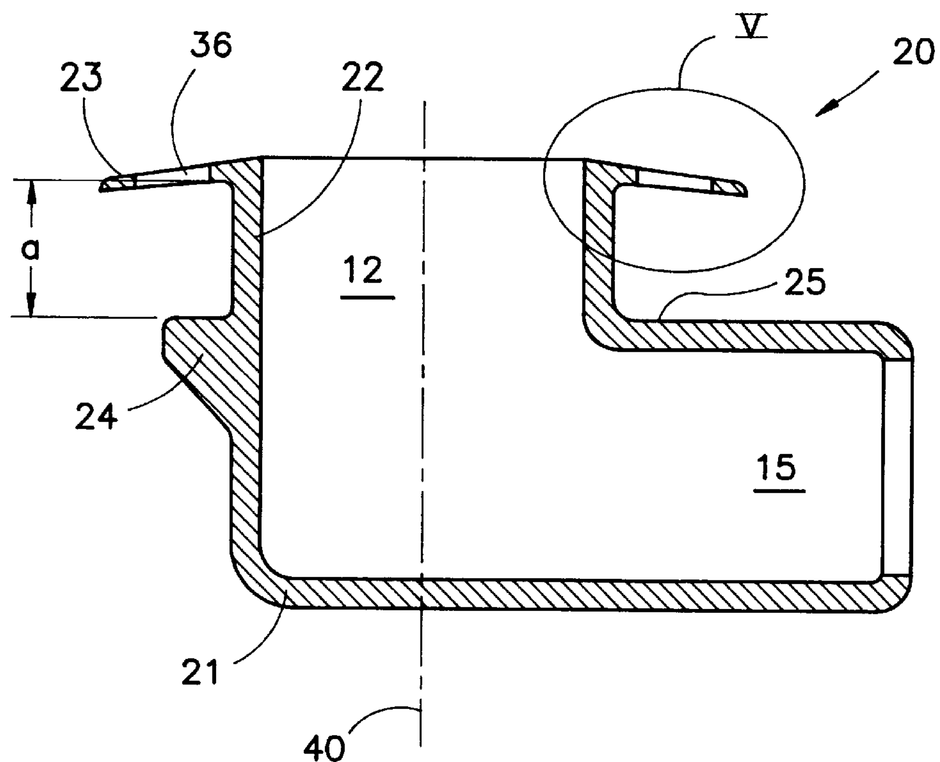
FIG. 4 is a sectional view of the fixation element taken along line IV—IV in FIG. 3.
Figure 5:
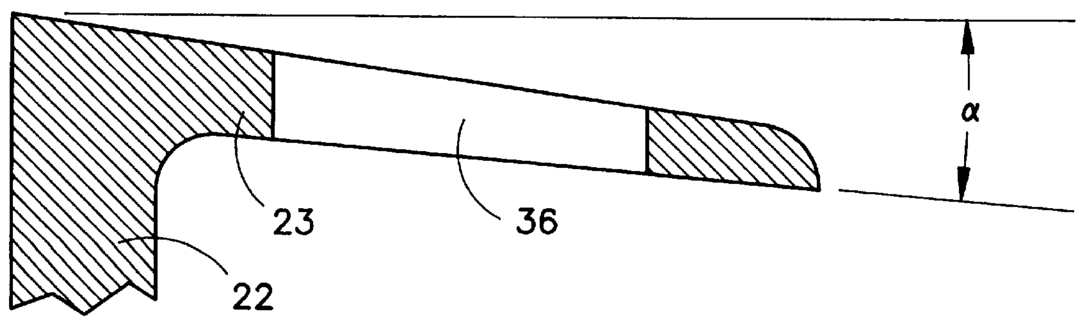
FIG. 5 is an enlarged view of the encircled region of the fixation element V shown in Fig. 4.

In the implantation of microphone 10 encased within fixation element 20, flange parts 23, 24, and 25 provide for alignment of the acoustic inlet membrane 13 and the housing leg 15 parallel to the bony wall 29 of the auditory canal in a position in which acoustic inlet membrane 13 is essentially flush with the side 33 of the wall 29 of the auditory canal which faces the skin 30 of the auditory canal 31. In addition, tipping of microphone 10, for example, by a force exerted accidently in the implantation process on microphone housing 11 and/or feed line 17 is effectively prevented. Fixation element 20 holds the microphone securely at the implantation site without the need for additional measures or means, for example, bone cement. If necessary, the microphone can be turned during implantation after insertion of cylindrical sleeve part 22 into hole 28 around the axis 40 of cylindrical housing part 14 (FIG. 4).

Fixation element 20 is suitably an injection molded part which holds microphone housing 11. A biocompatible plastic with a Shore A hardness of 20 to 70 is especially suitable as the material for fixation element 20. It can especially be made of such materials as silicones or polyurethanes.

Figure 7:
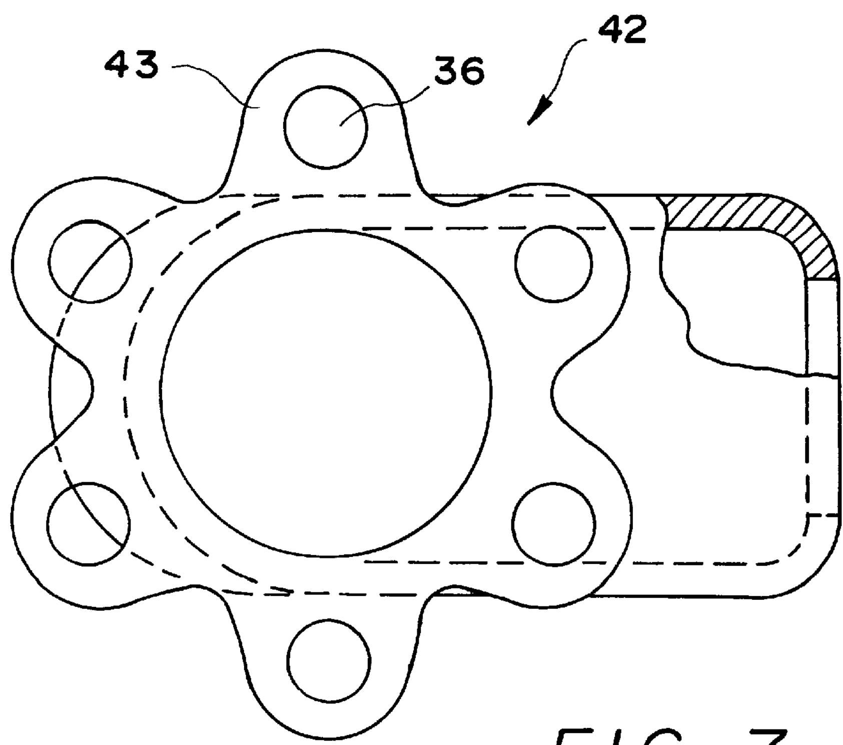
FIG. 7 is a plan view similar to FIG. 3 for a fixation element according to a modified embodiment.

The modified embodiment of fixation element 42 as shown in FIG. 7 differs from fixation element 20 explained above essentially only in that the flange parts which are located in the implanted state between wall 29 and skin 30 of the auditory canal are not formed by an annular flange 23, but by a series of flange segments 43 that are distributed in the peripheral direction around the cylindrical sleeve part 22. In this case, the flange segments 43, as shown, can be provided with openings 36. These openings, however, can also be dispensed with, especially when, as a result of the shape of the flange parts, nutrient transport between wall 29 and skin 30 of the auditory canal is ensured.

Figure 8:
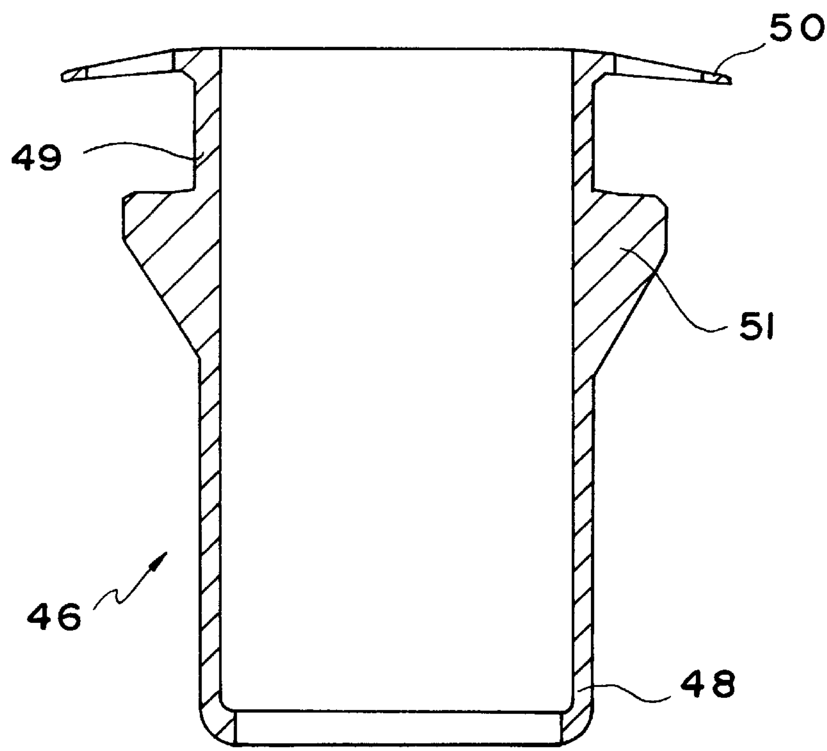
FIG. 8 is a cross-sectional side view of a fixation element according to another modified embodiment.

FIG. 8 shows a further modified embodiment of the fixation element which is labeled 46 throughout and which is suitable for microphones having a single-leg, cylindrical microphone housing. Fixation element 46, in turn, has a sleeve 48 which surrounds the cylindrical part of the microphone housing with cylindrical sleeve part 49 and which has projecting flange parts 50 and 51 shown in FIG. 1 which can be placed against the side 33 facing the skin 30 of the auditory canal 31, and against the side 34 of wall 29 facing away from the skin of the auditory canal. Flange part 50 can be designed especially according to the flange ring 23 of FIGS. 2–6, or can be formed as flange segments 43 as shown in FIG. 7. Flange part 51 can feasibly be formed as annular collar.

Figure 6:
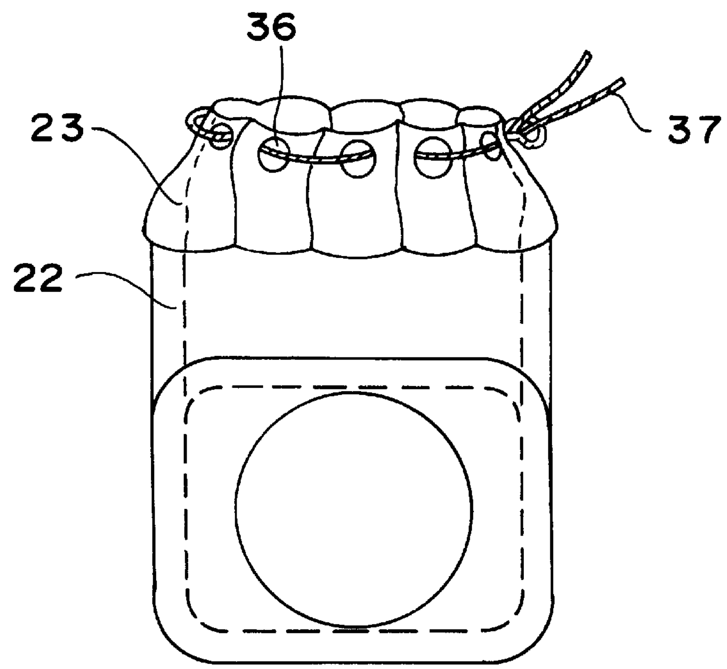
FIG. 6 is a view similar to that of FIG. 2, but, with the annular flange being shown in a state in which it is being prepared for implantation.
Figure 9:
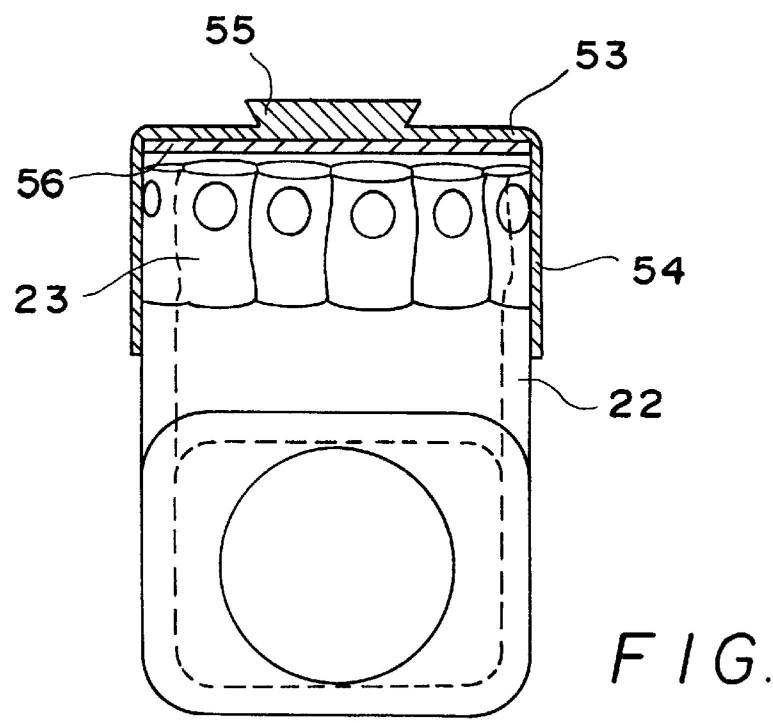
FIG. 9 is a view similar to that of FIG. 6, but, showing a cap being seated for holding back the flange parts before and during the implantation.

FIG. 9 shows a view similar to FIG. 6, but instead of thread 37, a cap is shown as being provided for retaining the flange parts 23, 43 or 50 before and during implantation. Cap 53 is thin-walled, at least in the region of its hollow cylindrical part 54, such that, together with cylindrical sleeve part 22 or 49, it can be inserted into hole 28 and then can be withdrawn from auditory canal 31 releasing flange parts 23, 43 or 50. To facilitate grasping of cap 53 with tweezers or the like, on its closed side, the cap bears a nipple 55. A relatively stiff and hard plate 56 is advantageously inserted into the hollow cylindrical part 54 of cap 53. Cap part 54 is preferably elastically stretchable to a limited degree. It must be possible to sterilize the cap material; otherwise, a host of materials, especially metals and plastics, are suitable cap materials. Cap 53 provides for outstanding protection of acoustic inlet membrane 13, especially when it is equipped with plate 56.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as are encompassed by the scope of the appended claims.

We claim:

1. Fixation element for an implantable microphone having a cylindrical housing part provided with an acoustic membrane which is insertable into a hole which crosses a rear bony wall of the auditory canal of a user, said fixation element comprising a sleeve which has a cylindrical sleeve part for surrounding the cylindrical housing part of the implantable microphone, in use, and which has projecting, elastic flange parts which are engageable against a side of the wall of the auditory canal which faces skin of the auditory canal.

2. Fixation element as claimed in claim 1, wherein said sleeve is provided with additional projecting flange parts which are positioned for placement, in use, against a side of the bony wall of the auditory canal facing away from the skin of the auditory canal when the elastic flange parts are engaged against the side of the wall of the auditory canal which faces skin of the auditory canal.

3. Fixation element as claimed in claim 2, wherein the sleeve is part of a casing which, in use, substantially entirely surrounds the microphone except for the acoustic membrane.

4. Fixation element as claimed in claim 2, further comprising a holder which holds the elastic flange parts in a bent position against an elastic restoring force of the flange parts before implantation and which allows insertion of the flanges through the hole of the wall of the auditory canal.

5. Fixation element as claimed in claim 4, wherein the elastic flange parts are composed and dimensioned such that, after removal of holder, they spring into a position in which they project essentially radially away from the cylindrical sleeve part.

6. Fixation element as claimed in claim 5, wherein the holder comprises a thread, which is severable in the course of implantation.

7. Fixation element as claimed in claim 5, wherein the holder is cap which is placable on the flange parts in the bent position thereof.

8. Fixation element as claimed in claim 2, wherein the entire sleeve is made of a biocompatible elastic material.

9. Fixation element as claimed in claim 8, wherein at least the cylindrical sleeve part if made from a material having a Shore A hardness from 20 to 70.

10. Fixation element as claimed in claim 8, wherein at least the cylindrical sleeve part is made from a material selected from the group consisting of silicones and polyurethanes.

11. Fixation element as claimed in claim 2, wherein the elastic flange parts are formed as an annular flange which projects away from cylindrical sleeve part in an essentially radial direction in a unstressed state.

12. Fixation element as claimed in claim 11, wherein elastic flange parts are provided with openings.

13. Fixation element as claimed in claim 2, for a microphone with a multi-leg microphone housing having a first housing leg forming a cylindrical microphone housing part and a second housing leg which is set back by a distance corresponding to a thickness of the rear bony wall of the auditory canal relative to the plane of acoustic inlet membrane; wherein the sleeve, in addition to said sleeve part, is provided with a second portion which jackets the second housing leg of the microphone, in use, said portion forming at least one said additional projecting flange parts.

14. Fixation element as claimed in claim 13, wherein a collar which projects from the cylindrical sleeve part on a side diametrically opposite from said portion comprises another of said additional projecting flange parts.

15. Fixation element as claimed in claim 1, wherein the elastic flange parts are angled toward the sleeve part.

16. Fixation element as claimed in claim 15, wherein the elastic flange parts have a wall thickness which decreases in a radially outward direction.

17. An implantable microphone assembly comprising an implantable microphone having a cylindrical housing part provided with an acoustic membrane which is insertable into a hole which crosses a rear bony wall of the auditory canal of a user, and a fixation element comprising a sleeve which has a cylindrical sleeve part which surrounds the cylindrical housing part of the implantable microphone, and which has projecting, elastic flange parts which, in use, are engageable against a side of the wall of the auditory canal which faces skin of the auditory canal.

18. Implantable microphone assembly as claimed in claim 17, wherein said sleeve is provided with additional projecting flange parts which are positioned for placement, in use, against a side of the bony wall of the auditory canal facing away from the skin of the auditory canal when the elastic flange parts are engaged against the side of the wall of the auditory canal which faces skin of the auditory canal.

19. Implantable microphone assembly as claimed in claim 17, wherein said microphone has a multi-leg microphone housing, a first leg of the housing forming the cylindrical microphone housing part and a second leg of the housing being back by a distance corresponding to a thickness of the rear bony wall of the auditory canal relative to the plane of acoustic inlet membrane; wherein the sleeve, in addition to said sleeve part, is provided with a portion which jackets the second housing leg of the microphone, said portion forming at least one of said additional projecting flange parts.

20. Method of implanting a microphone in a hole in a wall of an auditory canal of a user, comprising the steps of:

producing a hole in a wall of an auditory canal of a user;

providing an implantable microphone assembly comprising an implantable microphone having a cylindrical housing part provided with an acoustic membrane which is insertable into a hole which crosses a rear bony wall of the auditory canal of a user, and a fixation element comprising a sleeve which has a cylindrical sleeve part which surrounds the cylindrical housing part of the implantable microphone, and which has projecting, elastic flange parts which, in use, are engageable against a side of the wall of the auditory canal which faces skin of the auditory canal;

bending the elastic flange parts into a bent position against an elastic restoring force of the flange parts before implantation and applying a holder to the flange parts which allows insertion of the flanges through the hole of the wall of the auditory canal; and inserting the microphone assembly through said hole and removing the holder, and allowing the elastic flange parts to spring into a position in which they project essentially radially away from the cylindrical sleeve part between the wall of the auditory canal which faces skin of the auditory canal and the skin of the auditory canal.

* * * * *